United States Patent [19]
Weller

[11] Patent Number: 5,389,784
[45] Date of Patent: Feb. 14, 1995

[54] ION CYCLOTRON RESONANCE CELL

[75] Inventor: Robert R. Weller, Aiken, S.C.

[73] Assignee: The United States of America as represented by the United States Department of Energy, Washington, D.C.

[21] Appl. No.: 64,887

[22] Filed: May 24, 1993

[51] Int. Cl.[6] .............................................. H01J 49/20
[52] U.S. Cl. ...................................... 250/291; 250/281
[58] Field of Search ............... 250/291, 282, 290, 281, 250/292, 288

[56] References Cited

U.S. PATENT DOCUMENTS

| | | | |
|---|---|---|---|
| 3,505,516 | 4/1970 | Gielow | 250/291 |
| 3,677,642 | 7/1972 | Baldeschweiler | 356/72 |
| 3,937,955 | 2/1976 | Comisarow et al. | 250/283 |
| 4,535,235 | 8/1985 | McIver, Jr. | 250/282 |
| 4,581,533 | 4/1986 | Littlejohn et al. | 250/282 |
| 4,602,342 | 7/1986 | Gottlieb et al. | 250/339 |
| 4,739,165 | 4/1988 | Ghaderi et al. | 250/290 |
| 4,931,640 | 6/1990 | Marshall et al. | 250/291 |
| 5,089,702 | 2/1992 | Alleman et al. | 250/291 |

*Primary Examiner*—Jack I. Berman
*Assistant Examiner*—James Beyer

*Attorney, Agent, or Firm*—Brian R. Tumm; Harold M. Dixon; William R. Moser

[57] ABSTRACT

An ion cyclotron resonance cell having two adjacent sections separated by a center trapping plate. The first section is defined by the center trapping plate, a first end trapping plate, and excitation and detector electrodes. The second section includes a second end trapping plate spaced apart from the center plate, a mirror, and an analyzer. The analyzer includes a wavelength-selective light detector, such as a detector incorporating an acousto-optical device (AOD) and a photodetector. One or more ion guides, grounded plates with holes for the ion beam, are positioned within the vacuum chamber of the mass spectrometer between the ion source and the cell. After ions are trapped and analyzed by ion cyclotron resonance techniques in the first section, the ions of interest are selected according to their mass and passed into the second section for optical spectroscopic studies. The trapped ions are excited by light from a laser and caused thereby to fluoresce. The fluorescent light emitted by the excited ions is reflected by the mirror and directed onto the detector. The AOD is scanned, and the photodetector output is recorded and analyzed. The ions remain in the second section for an extended period, enabling multiple studies to be carried out on the same ensemble of ions.

20 Claims, 2 Drawing Sheets

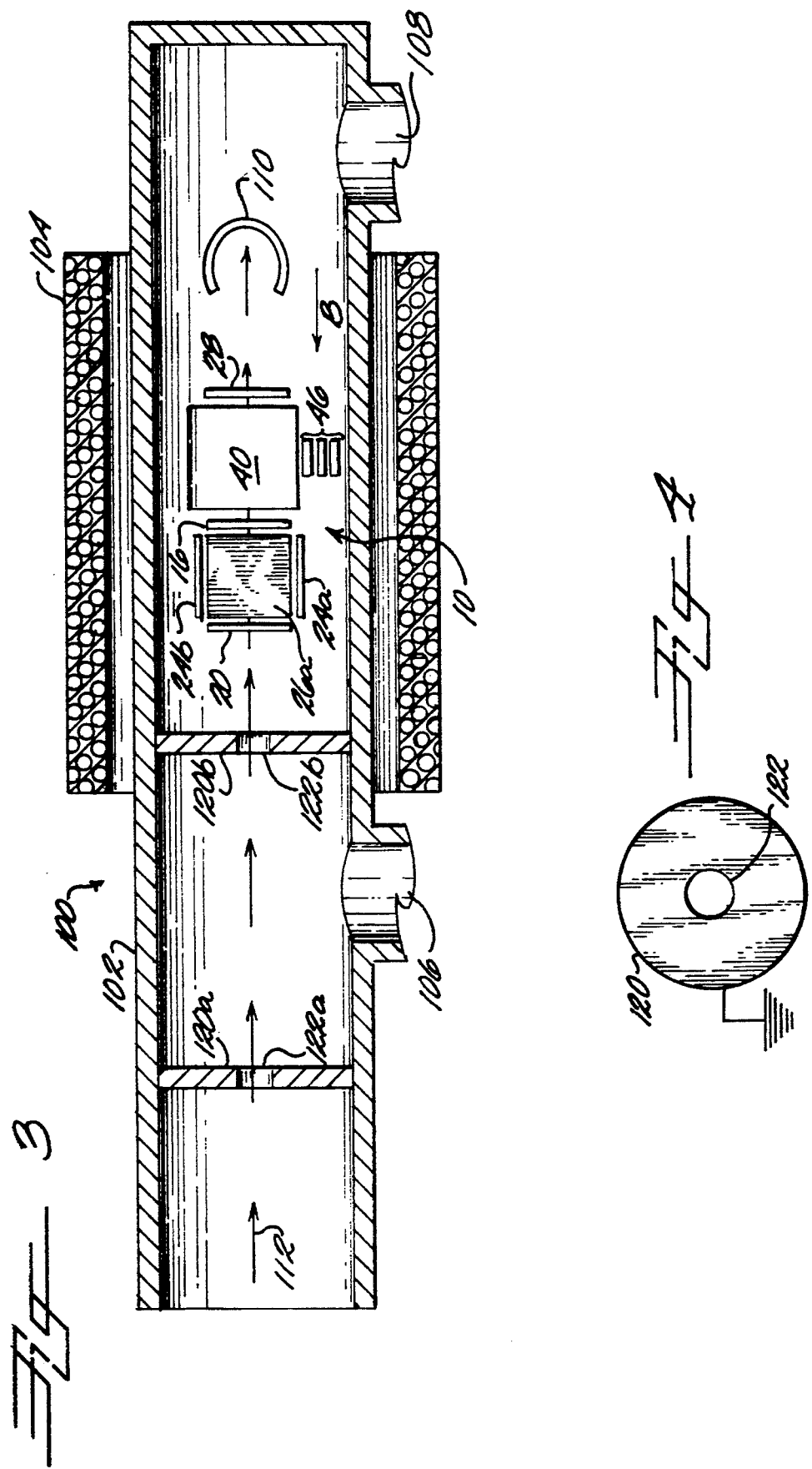

ION CYCLOTRON RESONANCE CELL

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to mass spectrometry. In particular, the present invention relates to an ion analyzer cell for use in ion cyclotron resonance mass spectrometry.

2. Discussion of Background

Ion cyclotron resonance mass spectroscopy (ICR-MS) is a sensitive technique for detecting gaseous ions. ICR-MS is based on the well known phenomenon that the motion of ions in a static magnetic field is constrained to a circular orbit in the plane perpendicular to the direction of the field. Ion motion is unrestrained in directions parallel to the field. The frequency of the circular motion is given by $\omega_c = (q/m)B$, where q is the charge of the ions, m their mass, and B the magnetic field strength. If the field strength is known, the mass-to-charge ratio of the ions can be determined from measurements of the resonance frequency $\omega_c$.

If a group of ions is subjected to a magnetic field and an oscillating electric field perpendicular to the magnetic field, those ions having an orbital frequency in resonance with the frequency of the electric field will absorb energy from the electric field and accelerate to a larger orbit; those with different frequencies will not. This behavior is used to distinguish the resonant ions from the non-resonant ions. The mass spectrum of a sample can be obtained by varying the frequency of the electric field, the field strength of the magnetic field, or both, so as to bring ions of differing mass-to-charge ratios into resonance with the electric field.

Several types of ICR-MS are available. For example, a gaseous sample may be bombarded with electrons to generate ions. The ions are directed through a region where they are subjected to mutually perpendicular static magnetic and oscillating electric fields. The ions ultimately strike a collector plate, and the resulting ion current is measured and recorded. In another type of ICR-MS, ions having a resonant frequency equal to the frequency of the oscillating electric field are accelerated and the resultant power absorbed from the electric field is measured. The measured power is related only to the resonant ions.

A disadvantage of these systems is that only a single frequency and a single mass-to-charge ratio can be detected at any given time. To obtain a mass-to-charge ratio spectrum, the magnetic field strength, the frequency of the electric field, or both, must be varied in step-wise fashion and the measurement repeated for each step. Fourier transform ion cyclotron resonance (FT-ICR) spectrometers such as that described by Comisarow, et al. (U.S. Pat. No. 3,937,955) provide faster data acquisition and detection efficiency than conventional ICR-MS systems. In an FT-ICR, ions are formed within an ion analyzer cell positioned in a homogeneous magnetic field. The ions are excited with a broad-band oscillating electric field pulse and their cyclotron motion is detected by amplification of the signal they induce in a set of receiver plates. Fourier transformation of the recorded signal provides a complete mass spectrum.

Ions for ICR-MS spectrometry are generated by a variety of techniques, including electron, ion, or laser beams directed at the sample to ionize it. The ions are held in an ion cyclotron resonance cell (analyzer cell; ICR cell) for analysis. The ICR cell is positioned in a vacuum chamber in a high strength, homogeneous magnetic field. The magnetic field prevents the ions from escaping in a direction perpendicular to the field, and a low voltage (trapping voltage) is applied to the end plates (trapping plates) of the cell to prevent the ions from escaping in the direction parallel to the field. In addition to the end trapping plates, ICR cells have paired side plates serving as excitation electrodes and detector electrodes. Grounded screens may be provided within the cell, just inside the end trapping plates, to reduce the electrostatic field in the cell resulting from the application of a potential to the end trapping plates (Marshall, et al., U.S. Pat. No. 4,931,640). ICR cells are available in several different geometries, including cubic, cylindrical, orthorhombic, hyperbolic, and multi-sectional cells.

For optimum performance, ICR-MS systems—including FT-ICR systems—must be operated at high magnetic field strengths and low pressures. Both the mass resolution and sensitivity of the system degrade seriously if the pressure in the ICR cell is higher than about $1 \times 10^{-6}$ torr. In most ICR-MS systems, the samples to be analyzed are introduced to the ICR cell where they are ionized by any of variety of techniques, including electron impact, laser desorption, and so forth. High speed pumping systems are needed to maintain high vacuum conditions at the analyzer cell. The geometry of available high strength, superconducting magnets severely restricts access to the ICR cell and consequently the placement of ion generation devices. Typical vacuum chambers inside a superconducting magnet are on the order of 4"–5" in diameter. Collisional damping of the signal, resulting from sample ionization at moderate pressures ($10^{-8}$–$10^{-5}$ torr) and analysis in the same cell, reduces the mass resolution and sensitivity of the system. In addition, an ICR cell can contain only a limited number of ions before their space charge seriously degrades the performance of the cell.

These problems are addressed by a multi-sectional ICR cell, wherein samples are introduced and ionized in one section, and analysis is performed in another section. Ions migrate between sections through a conductance limit plate that allows the maintenance of a pressure differential between the cell sections (Littlejohn, et al., U.S. Pat. No. 4,581,533). This arrangement reduces collisional damping in the analysis cell, but does not fully address the sample handling problems resulting from ion production within the bore of the magnet.

Another approach involves the use of external ion sources, where the ions are generated outside the magnetic field and transferred to the ICR cell. For example, McIver, Jr. (U.S. Pat. No. 4,545,235) uses a quadruple mass filter to inject ions from an external source into an ICR-MS system. The ions are injected parallel to the applied magnetic field and are trapped in the ICR cell for relatively long time periods during which analyses are performed. Electrostatic lenses or pulsed high voltage lenses are used to direct ions from an external source to an ICR cell, such as in the apparatus described by Ghaderi, et al. (U.S. Pat. No. 4,739,165). These arrangements are complex and increase the size and cost of the overall system. Without careful shielding, electrical interference from a quadrupole or electrostatic lens can affect the detection circuitry of the ICR cell.

FT-ICR is the highest resolution mass spectrometry technique currently available. When used with a laser for inducing fluorescence of the ions, FT-ICR is an ideal technique for identification and characterization of small samples, including but not limited to analysis of trace contaminants in micro-electronic devices. However, laser induced fluorescence (LIF) is difficult to carry out, due to low ion concentrations, interference from stray light or scattered light from the irradiating beam, the small amounts of light produced, and the operating constraints imposed by ion sources. Similar problems are encountered in applications of other mass spectrometric techniques, including collision-activated dissociation and laser photodissociation.

SUMMARY OF THE INVENTION

According to its major aspects and broadly stated, the present invention is an ion cyclotron resonance cell (ICR cell). The cell has two adjacent sections or compartments, with a center trapping plate positioned between the sections. The first section is defined by a plurality of electrode plates enclosing a predetermined volume, including the center trapping plate and an opposing, first end trapping plate. The second section includes a second end trapping plate spaced apart from the center plate, a collection mirror, and a light detector assembly. The trapping plates have apertures to allow passage of ion and laser beams therethrough.

The ICR cell is positioned in the vacuum chamber of an ICR-MS system, preferably a system having an external ion source. The trapping plates are oriented generally perpendicular to the direction of a substantially constant and uniform magnetic field. An electrostatic trapping potential is applied to the trapping plates of the first section, restricting ion movement to the first section. Grounded ion guides within the vacuum chamber direct and guide the ion beam to the cell. Ions are mass-selected in the first section and transferred to the second section. A trapping potential applied to the trapping plates of the second section confines the mass-selected ions. The trapped ions are excited in order to cause them to emit light, and the mirror directs at least a portion of the emitted light toward the detector, which produces an output related to the amount of light detected. The detector output is recorded and analyzed according to conventional techniques. The ions remain in the second section for an extended period, enabling multiple optical spectroscopic experiments to be carried out on the same group of ions.

An important feature of the present invention is the first section of the ICR cell. The first section includes electrode plates serving as excitation and detector electrodes, and two trapping plates that restrict ion movement along the direction of the magnetic field applied to the vacuum chamber. Ions may be mass selected by conventional ICR-MS techniques in the first section and transferred to the second section for optical spectroscopic studies. In addition, the first section may be used for conventional ICR-MS or FT-ICR measurements.

Another feature of the present invention is the second section of the ICR cell. The second section includes a trapping plate spaced apart from the center plate, a mirror positioned generally between the center trapping plate and the second end trapping plate, and a light detector assembly. The mirror is shaped to effectively collect and direct light from the second section onto the detector assembly. The detector assembly includes a tunable filter, preferably a sensitive, wavelength-selective device such as an acousto-optical device (AOD) or acousto-optical tunable filter (AOTF). The wavelength of the light transmitted by an AOD is a function of the audio frequency applied across a crystal. The light output of the AOD is directed onto a photodetector. The detector assembly may include a plurality of AODs and photodetectors arranged to maximize the light-collecting capability of the assembly. If desired, the detector assembly can include other components such as lenses to help direct light onto the AOD.

The ions transferred into the second section are largely confined to or about the longitudinal axis of the ICR cell, so the ions are readily excited by a laser beam directed along the axis. The laser beam passes completely through the cell, largely eliminating interference effects due to stray and scattered light. Since the ions are concentrated along the longitudinal axis of the cell, the mirror reflects a substantial portion of the emitted light onto the detector, thereby maximizing the detector output signal.

An additional feature of the present invention is the ion guide. One or more grounded ion guides are positioned within the vacuum chamber, between the external ion source and the ICR analyzer cell. The guides maintain the focus of the ion beam as it moves between the ion source and the ICR cell. Surprisingly, the ion guides improve the ion transfer efficiency of the mass spectrometer system by at least a factor of two, thereby reducing the need for costly and complex ion transfer optics such as quadrupoles and pulsed high voltage lenses.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 3 is a cross-sectional view of the vacuum chamber of an ICR-MS system, showing ion guides and an ion cyclotron resonance cell according to the present invention; and FIG. 4 is an ion guide according to a preferred embodiment of the present invention.

DETAILED DESCRIPTION OF A PREFERRED EMBODIMENT

Figure 1:
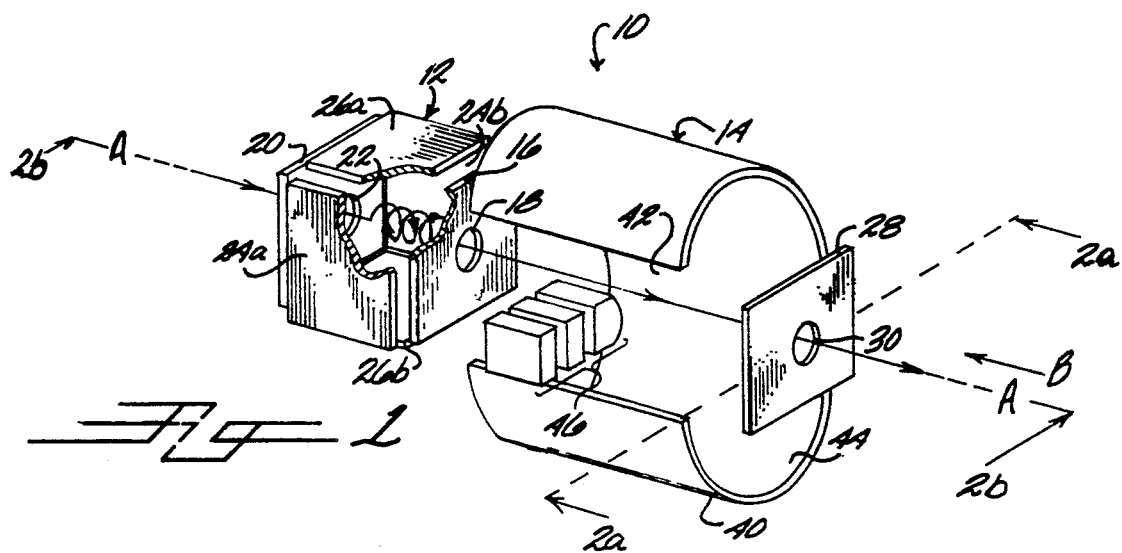
FIG. 1 is a perspective, partially cut-away view of an ion cyclotron resonance cell according to a preferred embodiment of the present invention.

Referring now to FIG. 1, there is shown an ion cyclotron resonance cell according to a preferred embodiment of the present invention. ICR cell 10 has longitudinal axis A, and two sections 12 and 14. Center trapping plate 16 is positioned between sections 12 and 14. Plate 16 has central aperture 18.

First section 12 has first end trapping plate 20 with central aperture 22. Center plate 16 and first end plate 20 form a pair of opposing, spaced-apart trapping plates positioned generally perpendicular to longitudinal axis A. Opposing side plates 24a, 24b serve as excitation electrodes, and top and bottom plates 26a, 26b serve as detector electrodes. Excitation electrodes 24a, 24b are connected to excitation control circuitry (not shown). Similarly, detector electrodes 26a, 26b are connected to detector circuitry (not shown).

Second section 14 includes second end trapping plate 28 with central aperture 30. Trapping plate 28 is generally perpendicular to axis A, so that plate 28 and center plate 16 form a pair of opposing, spaced-apart trapping plates. Collection mirror 40 is positioned between center plate 16 and trapping plate 28. Mirror 40 has open end 42 and inner reflecting surface 44.

Figure 2A:
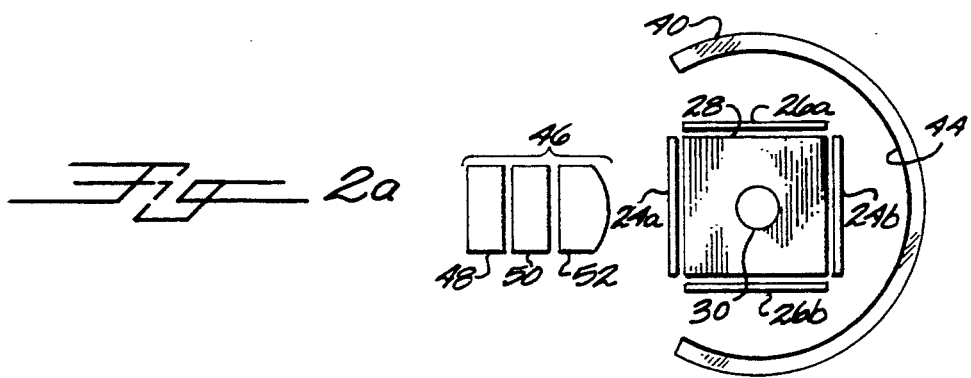
FIG. 2a is a cross-sectional view of the ion cyclotron resonance cell along line 2a—2a of FIG. 1.

A light detection assembly, represented schematically as assembly 46, is positioned at or near the focal point of mirror 40 (FIG. 2a). Assembly 46 includes photodetector 48 and tunable filter 50, preferably an acousto-optical device (AOD) or acousto-optical tunable filter (AOTF). (As used hereinafter, the term "AOD" refers to tunable filters, including but not limited to AODs and AOTFs.) As is known to those skilled in the art, AOD devices are extremely rapid, wavelength-selective light filters. The wavelength of the light transmitted by an AOD is proportional to the audio frequency applied across the device. The device is "tuned" or scanned over a range of audio frequencies corresponding to a range of light wavelengths. The output of device 50 is directed onto photosensitive detector 48. The output of photodetector 48 is connected to any suitable signal recording and analysis system (not shown). Detector assembly 46 may have a single AOD device and photodetector as shown in FIGS. 1 and 2a, or a plurality of AOD devices and photodetectors arranged to maximize the light-collecting capability and output signal of assembly 46. If desired, assembly 46 also includes collection optics such as lens 52 to help focus light onto AOD 50.

Alternatively, detector assembly 46 may be positioned remotely from ICR cell 10. For example, optical fibers may be used to transmit light from section 14 to assembly 46. However, detector 46 is preferably located in the vicinity of section 14 in order to minimize transmission losses.

Figure 2B:
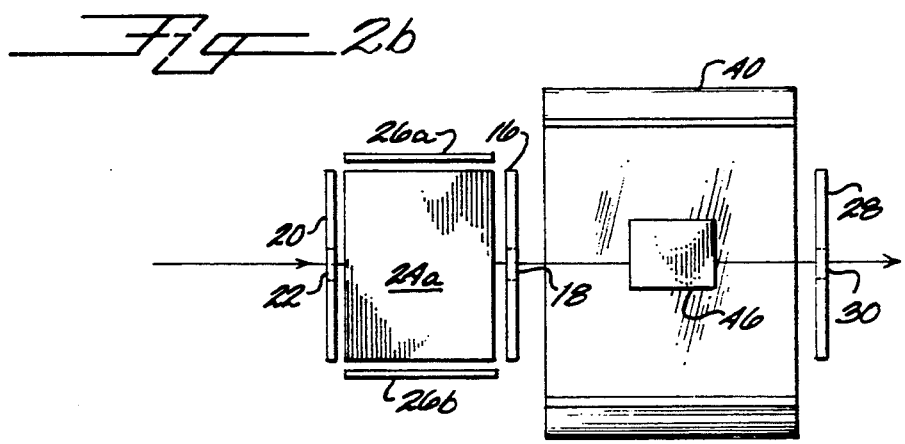
FIG. 2b is a side view of the ion cyclotron resonance cell along line 2b—2b of FIG. 1.

Mirror 40 is positioned generally between center trapping plate 16 and second end trapping plate 28, as best seen in FIGS. 1 and 2b. Mirror 40 is shaped to receive light from second section 14 and direct at least a portion of the light onto AOD 50. Mirror 14 may be approximately parabolic or partial-cylindrical, or some other shape that effectively directs light onto AOD 50. For most effective light collection capability, mirror 40 closely encloses section 14. Thus, mirror 40 preferably has an inner radius somewhat larger than trapping plates 16, 20, and 28.

Other means for receiving light from section 14 may be used in place of mirror 40. Thus, an array of optical fibers or photodetectors surrounding section 14 could transmit light to a suitable detector.

Section 12 of ICR cell 10 has a predetermined volume defined by trapping plates 16 and 20, and electrode plates 24a, 24b, 26a, 26b. Section 12 may be approximately cubical as shown in FIG. 1, or assume other geometric configurations, including cylindrical or hyperbolic forms, without departing from the spirit of the present invention. Similarly, section 14 has a volume defined approximately by mirror 40 and trapping plates 16 and 28.

Center trapping plate 16 is approximately equidistant from end plates 20 and 28. However, the relative position of plate 16 between plates 20 and 28, as well as the separation of plates 20 and 28, may be varied depending on the configuration of the mass spectrometer and the amount of light reaching detector 46.

ICR cell 10 is dimensioned for use within the vacuum chamber of an ICR-MS apparatus. Typical vacuum chambers are on the order of 4"-5" (about 10.2-12.7 cm) in diameter. Therefore, the cross-section of cell 10, including mirror 40 and detector assembly 46, may be up to approximately 3" (about 7.6 cm) in diameter. Apertures 18, 22, and 30 are generally a few millimeters in diameter. The optimum dimensions of cell 10 depend on the particular dimensions and configuration of the spectrometry apparatus in which the cell will be used.

ICR cell 10 is preferably made of conductive, non-magnetic materials, including but not limited to stainless steel, molybdenum, copper and the like, and may be solid or mesh in structure. Similarly, trapping plates 16, 20, and 28 may be solid or mesh. Electrostatic shields in the form of mesh screens (not shown) may be positioned inside cell 10, proximate to plates 16, 20, and 28, respectively. The screen mesh preferably has a spacing such that the screens are substantially transparent to ions, yet shield the interior of cell 10 from electrostatic fields produced by trapping voltages.

In use, ICR cell 10 is maintained in a substantially constant and uniform magnetic field represented by arrow B. Magnetic field B is produced by any suitable magnet. Trapping plates 16, 20, and 28 are oriented generally perpendicular to magnetic field B and longitudinal axis A, with apertures 18, 22, and 30 aligned along axis A. Plates 16, 20, and 28 are connected to a trapping potential control (not shown) which selectively applies trapping potentials of the appropriate polarities and magnitudes to the plates.

FIG. 3 shows a partial, cross-sectional view of an ICR-MS apparatus incorporating an ICR cell according to the present invention. Apparatus 100 includes vacuum chamber 102. Magnet 104 produces a substantially constant and uniform magnetic field, indicated generally by arrow B, inside chamber 102. Magnet 104 is preferably a superconducting, solenoid magnet. Conduits 106, 108 are connected to high-performance vacuum pumps (not shown). Chamber 102 includes beam stop 110. ICR cell 10 is positioned within chamber 102, substantially as shown in FIG. 3.

ICR-MS apparatus 100 may be supplied with an internal ion source, that is, the sample to be analyzed is introduced into vacuum chamber 102 and ionized by an electron gun, a laser, or other source of ionizing energy. Due to the limited types of ionization suitable for use as internal sources, apparatus 100 is preferably operated with an external ion source, where ions are generated outside chamber 102 and transferred to the chamber and ICR cell 10 by well known means.

Most preferably, ions are generated outside vacuum chamber 102, introduced to chamber 102 by any suitable technique, aligned with magnetic field B and transferred to cell 10. By way of example, an ion beam represented by arrows 112 may be generated by laser desorption of the sample to be analyzed.

Grounded ion guides 120a, 120b are positioned within chamber 102. Ion guides 120a, 120b have central apertures 122a, 122b, respectively, as indicated in FIG. 4.

Guides 120 are electrostatic lenses, dimensioned to fit in vacuum chamber 102, and positioned in any convenient locations between the ion source and ICR cell 10. Guides 120 focus and guide beam 112 to ICR cell 10. The optimum number of guides 120, the locations of the guides, and the most effective size of apertures 122 are best determined by observation and a modest degree of experimentation for each particular ICR-MS.

Surprisingly, the use of one of more ion guides 120 improves ion transfer efficiency between the ion source and ICR cell 10 by at least a factor of two. The addition of guides 120 to ICR-MS apparatus 100 improves the performance of any external ion source used with the apparatus, and thereby reduces the need for costly and complex ion transfer optics such as quadrupoles and pulsed high voltage lenses. Guides 120 allow state-of-the-art laser and ion microprobes to be easily interfaced to ultra-high-resolution ICR-MS systems, especially FT-ICR systems. The guides may also be used to improve ion transfer efficiency in conventional mass spectrometry systems.

Chamber 102 is evacuated, and the appropriate temperature and pressure conditions are established in a well known manner. The sample to be analyzed is ionized and introduced into chamber 102 in the form of ion beam 112, aligned generally along axis A. Beam 112 is guided to ICR cell 10 by ion guides 120a, 120b. Alternatively, an internal source is used, wherein the sample is introduced into chamber 102 and ionized by an electron gun, a laser, or other source of ionizing energy.

Ions are trapped in first section 12 of ICR cell 10. The ions in beam 112 are free to move along in the direction of the magnetic field B. Ion motion in the plane perpendicular to the field is constrained, so the ions move in a helical path about axis A as indicated in FIG. 1. An electrostatic trapping potential applied to first end trapping plate 20 and center trapping plate 16 restricts ion movement to the region between these plates. The magnitude and polarity of the trapping potential depend on the polarity of the ions being investigated. Ion excitation and detection may take place in first section 12 by means well known in the art. Preferably, excitation and detection are such as are used in FTMS spectrometry.

After mass analysis in first section 12, the ions of interest are mass-selected and transferred to second section 14. Since the transferred ions enter section 14 through aperture 18 of center trapping plate 16, the ions are largely concentrated at or near longitudinal axis A of ICR cell 10. A trapping potential is applied to center plate 16 and second end trapping plate 28, confining the selected ions to section 14.

Optical and mass spectroscopic studies such as are known in ion cyclotron resonance spectrometry are carried out on the ions. Laser induced fluorescence (LIF) studies are performed in section 14; laser photodissociation and collision-activated dissociation (collision-induced dissociation) studies are performed in section 12. Light emitted by the ions is reflected by surface 44 of mirror 40 onto detector assembly 46, and AOD 50 is scanned over an audio frequency range corresponding to the wavelength range of the emitted light. The output of AOD 50 is directed to photodetector 48. The output of photodetector 48 is recorded and analyzed by any convenient means.

By way of example, LIF studies are carried out in section 14 by using a laser to excite the ions which subsequently undergo fluorescence. The apertures in ion guides 120 and trapping plates 16, 20, and 28 allow passage of the laser beam into section 14 along axis A. The ions in section 14 are concentrated at or near axis A, so laser excitation is a highly efficient method of inducing fluorescence. The fluorescing ions emit light that is reflected by mirror 40 onto detector assembly 46. AOD 50 is scanned and the output of photodetector 48 is recorded to obtain the spectrum of the emitted light.

The fluorescing ions are located generally near axis A of ICR cell 10. Mirror 40 preferably has a parabolic shape to receive light from the vicinity of axis A and direct the light onto detector 46, so the combination of mirror 40 and detector 46 thus enables a substantial portion of the light emitted by the ions to reach the detector. Therefore, ICR cell 10 efficiently uses low concentrations of ions such as are encountered in LIF of ions. Furthermore, the exciting laser beam passes through apertures 16 and 30 of section 14, and is absorbed by beam stop 110, largely eliminating interference effects due to stray and scattered light. The excited ions remain trapped in section 14 for an extended period, enabling multiple experiments to be carried out on the same ensemble of ions and allowing the use of standard signal averaging techniques. Space charge effects are avoided and the full dynamic range of detector 46 can be used to study the ions of interest.

Ion transfer efficiency between the source and ICR cell 10 is improved by a factor of two or more when the cell is used in conjunction with one or more ion guides 120 according to the present invention, further improving the efficiency of apparatus 100 for studies of low ion concentrations. Thus, for example, surface characterization studies can be carried out using laser and ion microprobes interfaced to ultra-high-resolution ICR-MS systems. ICR 10 may be used with a number of optical spectroscopic techniques, including but not limited to LIF.

When ICR cell 10 is used with an external ion source and ion guides 120 as described above, the relatively high pressures associated with sample separation and ionization are confined to the location of the external source. Maintenance of the high vacuum required for the mass and optical spectroscopic studies ($10^{-8}$ torr or lower) is simplified. The need for complex and expensive transfer systems such as quadrupoles and electrostatic lenses is reduced. If desired, however, an ICR cell according to the present invention may be used with an internal ion source or with other ion transfer systems.

It will be apparent to those skilled in the art that many changes and substitutions can be made to the preferred embodiment herein described without departing from the spirit and scope of the present invention as defined by the appended claims.

What is claimed is:

1. An ion cyclotron resonance cell for analyzing a beam of ions, said cell comprising:
    a plurality of electrode plates defining a first volume, said plurality of electrode plates including a pair of opposing trapping plates, said pair of opposing trapping plates each having a hole formed therein through which said beam of ions can move;
    an end trapping plate spaced apart from one trapping plate of said pair of trapping plates thereby defining a second volume therebetween and into which said ion beam moves;
    means in spaced relation to said second volume for causing said ion beam to fluoresce whereby said ion beam gives off light;

means in spaced relation to said second volume for collecting at least a portion of said light, said collecting means surrounding said second volume; and means in operating connection with said collecting means for analyzing said at least a portion of said light.

2. The ion cyclotron resonance cell as recited in claim 1, wherein said analyzing means is responsive to the intensity of said at least a portion of said light and produces an output signal related thereto.

3. The ion cyclotron resonance cell as recited in claim 1, wherein said analyzing means further comprises a wavelength-selective light detector.

4. The ion cyclotron resonance cell as recited in claim 1, wherein said analyzing means further comprises an acousto-optical device.

5. The ion cyclotron resonance cell as recited in claim 1, wherein said collecting means is a mirror formed to reflect said at least a portion of said light toward said analyzing means.

6. An ion cyclotron resonance cell for use with a remote source of ions, said cell comprising:

a plurality of electrode plates defining a first section, said first section temporarily confining said ions, at least one of said plurality of electrode plates having a hole formed therein for emitting said ions in a beam;

means for forcing said ions to exit said hole;

an end trapping plate spaced apart from said at least one of said plurality of electrode plates to define a second section, said beam entering said second section through said hole;

means in spaced relation to said second section for causing said beam to give off light; and means in spaced relation to said second section for collecting at least a portion of said light, said collecting means surrounding said beam; and means in optical communication with said collecting means for analyzing said at least a portion of said light.

7. The apparatus as recited in claim 6, wherein said collecting means is a mirror in spaced relation to said second section so that said mirror can reflect said light to said analyzing means.

8. The apparatus as recited in claim 6, wherein said analyzing means further comprises a tunable filter, said filter selectively transmitting light of a predetermined wavelength.

9. The apparatus as recited in claim 6, wherein said analyzing means further comprises an acousto-optical device.

10. The apparatus as recited in claim 6, wherein said light-collecting means further comprises a mirror, said mirror positioned and shaped to direct at least a portion of said collected light onto said analyzing means.

11. The apparatus as recited in claim 6, wherein said light-collecting means further comprises a mirror curved about said beam to have a parabolic cross section, said analyzing means laying on the focal point of said mirror so that said mirror can reflect at least a portion of said light onto said analyzing means.

12. The apparatus as recited in claim 6, further comprising means for guiding said ions into said first section.

13. The apparatus as recited in claim 6, further comprising a plurality of guides having holes formed therein, said guides being held at ground potential for guiding said ions into said first section.

14. The ion cyclotron resonance cell as recited in claim 6, wherein said causing means further comprises a laser directed at said ions so that light emitted by said laser excites said ions whereby said ions fluoresce.

15. An ion cyclotron resonance cell for use in a mass spectrometer, said cell having a longitudinal axis, said cell comprising:

a pair of opposing, spaced-apart trapping plates, said trapping plates laying in planes substantially perpendicular to said longitudinal axis;

a plurality of electrode plates, said electrode plates spaced apart from said longitudinal axis whereby the combination of said electrode plates and said pair of trapping plates form a first section, a first plate of said trapping plates having an entrance hole and an opposing, second plate of said trapping plates having an exit hole;

an end trapping plate, said end trapping plate laying in a plane substantially perpendicular to said longitudinal axis, said end trapping plate opposing said second plate and spaced apart therefrom to define a second section, said ions passing through said exit hole into said second section;

means in spaced relation to said first section for guiding ions through said entrance hole;

means in electrical connection with said plurality of electrode plates for mass-analyzing said ions in said first section, said mass-analyzing means analyzing said ions by ion cyclotron resonance methods;

a laser in spaced relation to said second section and adapted for directing laser light on said ions so that said ions are excited and fluoresce, thereby emitting light;

means in spaced relation to said exciting means for receiving at least a portion of said light, said receiving means surrounding said second section; and means responsive to said receiving means for analyzing said at least a portion of said light.

16. The ion cyclotron resonance cell as recited in claim 15, wherein said analyzing means produces an output signal indicative of the intensity of said at least a portion of said light.

17. The ion cyclotron resonance cell as recited in claim 15, wherein said receiving means further comprises a curved mirror that reflects said at least a portion of said light onto said analyzing means.

18. The ion cyclotron resonance cell as recited in claim 15, wherein said analyzing means further comprises an acousto-optical device.

19. The ion cyclotron resonance cell as recited in claim 15, wherein said receiving means further comprises a curved mirror that reflects said at least a portion of said light onto said analyzing means and said analyzing means further comprises:

a lens positioned to receive said at least a portion of said light;

an acousto-optical device in spaced relation to said lens, said lens focusing said at least a portion of said light onto said device; and a photodetector positioned to receive light from said acousto-optical device.

20. The ion cyclotron resonance cell as recited in claim 15, wherein said guiding means further comprises at least one plate spaced apart from said first section, held at ground potential with respect to said electrode plates and having a hole formed therethrough for said ions to pass.

* * * * *